(12) United States Patent
Mavor et al.

(10) Patent No.: US 7,979,117 B2
(45) Date of Patent: Jul. 12, 2011

(54) DEVICE AND METHOD FOR CONTROLLED DELIVERY OF ACTIVE SUBSTANCE INTO THE SKIN

(75) Inventors: Daniela Mavor, Tel Aviv (IL); Zvi Nitzan, Zofit (IL); Dov Tamarkin, Maccabim (IL); Giora Arbel, Kfar Saba (IL); Nurit Harel, Tel Aviv (IL); Yossi Gross, Moshav Mazor (IL)

(73) Assignee: Power Paper Ltd., Beit Shemesh (IL)

( * ) Notice: Subject to any disclaimer, the term of this patent is extended or adjusted under 35 U.S.C. 154(b) by 1053 days.

(21) Appl. No.: 10/493,386

(22) PCT Filed: Oct. 23, 2002

(86) PCT No.: PCT/IL02/00849
§ 371 (c)(1),
(2), (4) Date: Aug. 25, 2004

(87) PCT Pub. No.: WO03/035167
PCT Pub. Date: May 1, 2003

(65) Prior Publication Data
US 2004/0267189 A1    Dec. 30, 2004

Related U.S. Application Data

(60) Provisional application No. 60/330,526, filed on Oct. 24, 2001, provisional application No. 60/401,771, filed on Aug. 8, 2002.

(51) Int. Cl.
*A61N 1/30* (2006.01)
(52) U.S. Cl. .............................. 604/20; 429/127; 601/17

(58) Field of Classification Search .............. 604/20–22, 604/501, 890.1–892.1; 601/17
See application file for complete search history.

(56) References Cited

U.S. PATENT DOCUMENTS

| 4,474,570 | A | * | 10/1984 | Ariura et al. | 604/20 |
| 4,557,723 | A | * | 12/1985 | Sibalis | 604/20 |
| 5,213,568 | A | * | 5/1993 | Lattin et al. | 604/20 |
| 5,652,043 | A |   | 7/1997 | Nitzan | |
| 5,800,685 | A |   | 9/1998 | Perrault | |

(Continued)

FOREIGN PATENT DOCUMENTS
WO    WO 98/56458    12/1998
(Continued)

OTHER PUBLICATIONS

Glikfeld et al. "A New System for InVitro Studies of Ionthophoresis" Pharm. Res. vol. 5, pp. 443-446 (1998).

*Primary Examiner* — Theodore J Stigell
*Assistant Examiner* — Emily Schmidt
(74) *Attorney, Agent, or Firm* — Kenyon & Kenyon LLP

(57) ABSTRACT

An apparatus for dermal treatment of an active substance having certain physical properties having a flexible, wearable patch conformable to the contour of a skin surface and having: a first electrode adapted to communicate the active substance into the skin by application of an electrical current on the skin surface, a second electrode capable of closing an electrical circuit with the skin surface, a power source for providing a current and voltage connected through a conductive media to the first and second electrode, and an apparatus for substantially controlling penetration depth of the active substance by selecting at least one variable from a plurality of variables.

32 Claims, 5 Drawing Sheets

U.S. PATENT DOCUMENTS

| | | |
|---|---|---|
| 5,811,204 A | 9/1998 | Nitzan |
| 5,814,094 A * | 9/1998 | Becker et al. ............... 607/50 |
| 5,897,522 A | 4/1999 | Nitzan |
| 5,899,856 A | 5/1999 | Schoendorfer et al. |
| 5,919,762 A * | 7/1999 | Schweden et al. ............ 514/12 |
| 6,238,381 B1 | 5/2001 | Tapper |
| 6,266,560 B1 | 7/2001 | Zhang et al. |
| 6,288,104 B1 | 9/2001 | Gericke et al. |
| 6,291,677 B1 | 9/2001 | Vasudevan et al. |
| 6,294,582 B1 | 9/2001 | Jerussi |
| 6,477,410 B1 * | 11/2002 | Henley et al. .................. 604/20 |
| 6,615,078 B1 * | 9/2003 | Burson et al. .................. 604/20 |
| 6,706,032 B2 * | 3/2004 | Weaver et al. ................ 604/500 |
| 2002/0022040 A1 * | 2/2002 | Robinson et al. ............ 424/401 |
| 2002/0182485 A1 * | 12/2002 | Anderson et al. ............ 429/105 |
| 2003/0060797 A1 * | 3/2003 | Fischer ........................ 604/501 |

FOREIGN PATENT DOCUMENTS

| | | |
|---|---|---|
| WO | WO 00/53256 | 9/2000 |

* cited by examiner

DEVICE AND METHOD FOR CONTROLLED DELIVERY OF ACTIVE SUBSTANCE INTO THE SKIN

This application is a 371 national phase application of PCT/IL02/00849 filed on 23 Oct. 2002, claiming priority to U.S. provisional application No. 60/330,526 filed 24 Oct. 2001 and No. 60/401,771 filed 8 Aug. 2002, the contents of which are incorporated herein by reference in their entirety.

FIELD OF THE INVENTION

The present invention relates to a device and a method for controlled delivery of an active substance to a subject's skin.

BACKGROUND OF THE INVENTION

Much recent attention has been paid in the technical and patent literature to the delivery of substances, both pharmaceuticals and cosmetics, such as drugs and other beneficial agents, into patients by passive processes such as diffusion and osmosis and by active processes such as electrically induced iontophoresis, electrophoresis, electroosmosis and/or electroporation. Hereinafter, the term "iontophoresis" will collectively represent any of the terms iontophoresis, electrophoresis, electroosmosis and/or electroporation; and the term "iontophoretic" will encompass the respective adjectives. The ubiquitous nicotine patch designed to assist in quitting smoking has caused such forms of delivery of medication to be widely known. Indeed, there is now an extremely long list of pharmaceutical substances that are routinely administered transdermally and a similarly long list of devices and methods known in the art for administering same. A short but varied sampling includes the following: U.S. Pat. No. 6,294,582 which discloses a device for treating asthma transdermally; U.S. Pat. No. 5,899,856 which discloses a dermal patch for detecting alcohol consumption; U.S. Pat. No. 6,291,677 which teaches the transdermal administration of antiviral protease inhibitors; U.S. Pat. No. 6,266,560 which discloses the transdermal treatment of erectile dysfunction; U.S. Pat. No. 6,238,381 which discloses the transdermal delivery of antiviral, antibacterial and antiaging substances; and U.S. Pat. No. 6,288,104 which discloses the transdermal administration of substances for treating congestive heart failure.

Most present dermal patches, including those that function passively and those that function electrically, incorporate an active substance to be delivered. Such patches are specifically designed and/or configured to deliver a predetermined dosage of a specific substance, and that substance forms an integral part of the patch in question, i.e., the "nicotine patch". One drawback of such dermal patches, which are manufactured with a predetermined type and amount of substance therein, is that once the substance is depleted, the entire device is useless and must be discarded. This is a disadvantage because patches which employ electrically induced delivery techniques necessarily have components, e.g., batteries, electrodes, circuitry and other assemblies, which may be expensive and/or environmentally hazardous when discarded in large quantities. Also, in order to change dosage, patches of different dosages must be provided.

In iontophoresis, an electric current is used to drive ions of an active substance into or through the skin of a subject. Devices that deliver active substances using iontophoresis have been developed for many applications, most of which involve the delivery of pharmaceutical compounds through the subject's skin and into the circulatory system or other organs of a subject's body. Topical application of one or more active ingredient to the skin through the use of an iontophoresis device is called dermal treatment. Iontophoretic devices have taken two basic forms:

First, there are flexible, wearable devices such as transdermal patches. Most such devices include a small power source (such as an electrochemical cell), an electrode for delivering the active substance (i.e., a dispersing electrode), another electrode, and circuitry providing a small current through the electrodes and into the skin of the subject's tissue to be treated. The circuit is closed by contact with the subject's skin.

An advantage of such devices is their convenience. For example, with a transdermal patch, a subject can move around while still using the patch, and can use the patch at home. A drawback of such devices is that unless expensive and potentially bulky control elements are included, there is limited control over the delivery of the active substance, including the depth to which the active substance is delivered into the subject. This is not as important when delivery of pharmaceutical compounds is involved, since the object is generally to deliver the active substance through the skin and into the rest of the subject's body. However, precise depth control is more important for delivery of compounds used for cosmetic or dermatological applications, as the object is to deliver the active substance into the skin, but not through the skin.

The second basic form of iontophoretic devices are machines that include a separate base unit to which rigid electrodes are attached by cables. These machines are stationary, and are plugged into an electrical outlet. In operation, the electrodes connected to these machines are placed on the skin, which results in delivery of the active substance according to the same principles discussed above.

An advantage of these machines is that they may allow for some control of the delivery of the active substance by adjusting the parameters of the machine while it is in operation. For example, the rate of delivery could be increased by increasing the current density supplied by the machine. A drawback of such machines is that they are relatively inconvenient. The subject cannot move around while using such machines. Moreover, due to the cost of the machines, they generally cannot be used at home, but instead can only be used at a medical facility (for machines that deliver pharmaceutical compounds) or spa or beauty parlor (for machines that deliver cosmetics).

Another drawback of these machines is that the entire active electrode is not in contact with the subject's skin, which can result in varying amounts of active substance being delivered at different locations along the skin/electrode interface (e.g., greater amounts of active substance are delivered at those skin locations on the interface that are in contact with the active electrode for the greatest amount of time). This phenomenon is exacerbated in machines of this basic form that are used to deliver cosmetics by iontophoresis. An example of such a machine is the IONZYME™ DF 1998. Such machines may have the active electrode attached to a roller that is rolled back and forth over the skin of a subject, delivering dermatological and/or cosmetic ingredients at the momentary point of contact of those rollers with the skin.

Thus, there is a need for a thin, flexible and simple electrically active dermal patch that is easy to administer by the subject, versatile and capable of application with a range of substances and/or dosages and for a variety of purposes and that is simple in design and inexpensive to manufacture. There is also a need for a device, which is flexible and wearable on the one hand, but on the other hand allows for a uniform and precise depth control without the inclusion of an additional control element. Such a device would facilitate the delivery of active substances (such as cosmetics) that are most effective when delivered into the skin with minimal delivery through the skin, without sacrificing the basic convenience of a transdermal patch.

SUMMARY OF THE INVENTION

The present invention is generally directed to a device and method for iontophoretic delivery of an active substance into the skin wherein more of the active substance is retained in the skin than the amount of the active substance that penetrates through the skin. The invention includes a flexible, wearable patch that can conform and adhere to the skin surface of a person. The patch further includes a first and a second electrode connected to a wearable power source. The patch is adapted to deliver a formulation including at least one active substance.

According to one embodiment of the present invention there its provided a kit for introduction of current and/or voltage to a skin portion of a subject, the kit comprising (a) a dermal patch which comprises an electrochemical cell having at least two electrodes positioned on one side of the dermal patch for forming electrical contact with the skin portion of the subject; and (b) at least one retainer for retaining a conductive fluid for deposition on at least one of the electrodes and/or topical application onto the skin portion of the subject, wherein said retainer is not incorporated into the patch (said retainer may be an electric separator [hereinafter, "separator"]); the patch being designed and configured for delivering an electric current for introduction of current and/or voltage to the skin portion of the subject through the conductive fluid.

According to another aspect of the invention, the formulation may be included in a separator that is incorporated into the patch.

The separator may be a substrate including a porous material for retaining the formulation. Such a substrate is interposed between the at least one of the electrodes and the subject's skin and, upon application of current to the electrode, the patch can deliver a quantity of the active substance to the subject's skin. One example of such a substrate retaining a formulation including an active substance would be a soaked pad.

According to another aspect of the invention, the depth into the skin to which the active substance penetrates is controlled by carefully pre-selecting certain parameters of the patch, the formulation and the substrate, such as (i) the voltage and/or current applied to the electrodes, (ii) the pH, conductivity, viscosity, adhesiveness and active substance concentration of the formulation, and (iii) the size and density of the pores of the substrate. By pre-selecting these parameters, the patch is customized to deliver the active substance of the formulation to a certain depth within the subject without the need for the inclusion of a control element, which can adjust one or more of these parameters during the operation of the patch. For formulations in which the active substance is a cosmetic or dermatological agent, the parameters can be pre-selected to enhance the amount of the cosmetic or dermatological agent that is delivered into the skin but not through the skin.

BRIEF DESCRIPTION OF THE DRAWINGS

The various features of the invention will best be appreciated by simultaneous reference to the description that follows and the accompanying drawings, wherein like numerals indicate like elements, and in which.

DETAILED DESCRIPTION OF THE EMBODIMENTS OF THE INVENTION

Figure 1:
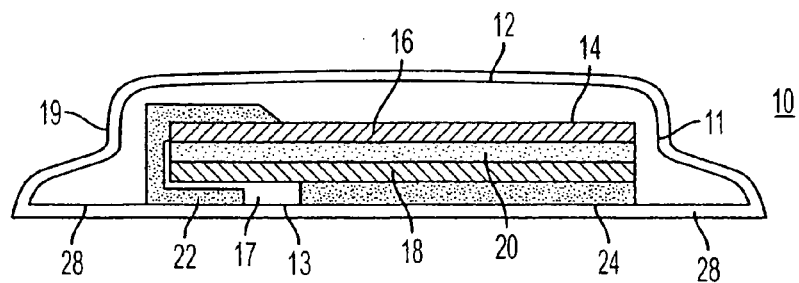
FIG. 1 is a cross sectional representation of one embodiment of the iontophoresis patch of the invention.

Reference is now made to FIG. 1, which shows a dermal patch in accordance with the teachings of the present invention, which is referred to herein below as patch 10. Patch 10 includes a top surface 12 and a skin contacting bottom surface 13, which together form patch body 11. Patch 10 is preferably fabricated from flexible materials, which enable surface 12 and/or 13 to conform to the contours of a subject's skin portion when patch 10 is applied thereon. It is understood that patch body 11 may be of any size and shape necessary according to the relevant application.

Patch 10 preferably further includes a skin attachment mechanism, which is preferably an adhesive layer 28, which serves for attaching patch 10 to a skin portion of the subject. Adhesive layer 28 covers at least a portion of bottom surface 13 of patch 10. Adhesive layer 28 preferably includes a biocompatible permeable pressure sensitive adhesive such as BIO-PSA™ from Dow Corning. Other examples of biocompatible adhesives will be readily apparent to those of ordinary skill in the art. Adhesive layer 28 may be useful for either a single attachment or repeated attachments.

Patch 10 includes therein an electrochemical cell 14, which is preferably a flexible thin electrochemical cell, most preferably an open, liquid state electrochemical cell. It is appreciated that patch 10 may employ any other electrochemical cell or power generating device that serves to provide the needed electric current for the relevant application. Numerous types of miniature power sources, both disposable and rechargeable, which can be incorporated into patch body 11 are known in the art.

According to a preferred embodiment of the present invention electrochemical cell 14 is a thin flexible electrochemical cell, which engages most of the entire volume of patch body 11. In the presently preferred embodiment, electrochemical cell 14 includes a positive pole layer 16, a negative pole layer 18 and an electrolyte layer 20 interposed therebetween. An example of a suitable thin and flexible electrochemical cell is described, for example, in U.S. Pat. Nos. 5,652,043, 5,897, 522 and 5,811,204, which are incorporated herein by reference. Briefly, the electrochemical cell described in the above identified U.S. patents is an open liquid state, electrochemical cell which can be used as a primary or rechargeable power source for various miniaturized and portable electrically powered devices of compact design. The cell comprises a first layer of insoluble negative pole, a second layer of insoluble positive pole and a third layer of aqueous electrolyte being disposed between the first and second layers and including (a) a deliquescent material for keeping the open cell wet at all times; (b) an electroactive soluble material for obtaining required ionic conductivity; and, (c) a water-soluble polymer for obtaining a required viscosity for adhering the first and second layers to the first layer.

Several preferred embodiments of the disclosed electrochemical cell include (i) engaging the electrolyte layer in a porous substance, such as, but not limited to, a filter paper, a plastic membrane, a cellulose membrane and a cloth; (ii) having the first layer of insoluble positive pole include manganese-dioxide powder and the second layer of insoluble negative pole include zinc powder; (iii) having the first layer of insoluble negative pole and/or the second layer of insoluble positive pole further include carbon powder; (iv) selecting the electroactive soluble from zinc-chloride, zinc-bromide, zinc-fluoride and potassium-hydroxide; (v) having the first layer of insoluble negative pole include silver-oxide powder and the second layer of insoluble positive pole include zinc powder and the electroactive soluble material is potassium-hydroxide; (vi) having the first layer of insoluble negative pole include cadmium powder and the second layer of insoluble positive pole include nickel-oxide powder and selecting the electroactive soluble material to be potassium-hydroxide; (vii) having the first layer of insoluble negative pole include iron powder and the second layer of insoluble positive pole include nickel-oxide powder and selecting the electroactive soluble material to be potassium-hydroxide; (viii) having the first layer of insoluble negative pole and the second layer, of insoluble positive pole include lead-oxide powder, then cell is charged by voltage applied to the poles and the electroactive soluble material is selected in this case to be sulfuric-acid; (ix) the deliquescent material and the electroactive soluble material can, be the same material such as zinc-chloride, zinc-bromide, zinc-fluoride and potassium-hydroxide; (x) the deliquescent material is selected from the group consisting of calcium-chloride, calcium-bromide, potassium-biphosphate and potassium-acetate; (xi) the water-soluble polymer can be polyvinyl alcohol, polyacrylamide, polyacrylic acid, polyvinylpyrolidone, polyethylenoxide, agar, agarose, starch, hydroxyethylcellulose and combinations and copolymers thereof; (xii) the water-soluble polymer and the deliquescent material can be the same material such as dextrane, dextrane-sulfate and combinations and copolymer thereof. Electrochemical cell 14 preferably incorporates any one or more of the embodiments described above. Preferred configurations for electrochemical cell 14 according to the present invention involve those combinations which are devoid of poisonous compounds.

Electrochemical cell 14 includes terminals serving as electrodes referred to hereinafter as positive electrode 22 and negative electrode 24 each of which being in electrical contact with positive pole layer 16 and negative pole layer 18, respectively. Electrodes 22 and 24 are electrically connected to electrochemical cell 14 using well known means, e.g., printed flexible circuits, metal foils, wires, electrically conductive adhesives or by direct contact. It is understood that measures are taken to avoid contact between the electrodes and between each of the electrodes and the opposite pole layer. In FIG. 1, the measure taken is the interposition of insulating element 17 formed of a dielectric material.

Electrodes 22 and 24 are electrically conductive and may be formed of a metal, e.g., a metal foil or metal deposited or painted on a suitable backing. Examples of suitable metals include aluminum, platinum, stainless steel, gold and titanium. Alternatively, electrodes 22 and 24 may be formed of a hydrophobic polymer matrix containing a conductive filler such as a metal powder/flakes, powdered graphite, carbon fibers or other known electrically conductive filler material.

Electrodes 22 and 24 can be applied to the cell and the entire cell can be manufactured by, for example, a suitable printing technology such as, but not limited to, silk print, offset print, jet printing, lamination, materials evaporation or powder dispersion. Accordingly, electrochemical cell 14 as described hereinabove is among the simplest of power sources.

It is appreciated that each of electrodes 22 and 24 may be of any size and shape, and located with respect to one another, in any arrangement, as may be required to cover the skin portion under treatment. Indeed, in accordance with a preferred embodiment of the present invention, electrochemical cell 14, in conjunction with electrodes 22 and 24, constitute the sole internal elements of patch 10. Accordingly, patch 10 is among the smallest and thinnest active practice patches and delivers the maximum power per unit of surface area.

Patch 10 of FIG. 1 is preferably supplied within a protective removable or reusable package, or liner, or cover 19, so as to provide physical protection and prolong shelf life prior to use. Patch 10 is designed and configured to be used with at least one, and preferably many, external substances. Such substances, described in detail hereinafter, are designed to be contained in a conductive fluid, also described in detail hereinafter. The conductive fluid is designed to be retained in at least one, preferably many, retainers. The combination of patch 10 and the retainer form a kit that may be retained by a patient for use for a variety of applications.

Reference is now made to FIGS. 2a-g, which show a range of exemplary retainers for retaining a conductive fluid. Such conductive fluid will generally be "pharmaceutically acceptable" or "physiologically acceptable" formulations for cosmetic or therapeutic use. As used herein, the terms "pharmaceutically acceptable" and "physiologically acceptable" refer to substances that can be administered to a subject, preferably without excessive adverse side effects (e.g., for a topically applied formulation, skin rash, irritation, etc.). Particular formulations include aqueous gels, cream, pastes, lotions, suspensions, emulsions and solutions or other liquid formulations suitable for topical application known in the art. In one embodiment, the conductive fluid is electrically conductive and adhesive hydrogel, suitable for use as a skin contact adhesive and, particularly, suitable for use as an electrical interface for electrodes of medical devices. The hydrogels are cationic acrylates and may be, for example, preferably made from acrylic esters of quaternary chlorides and/or sulfates or acrylic amides of quaternary chlorides. They can be formed by free radical polymerization in the presence of water, preferably by ultra-violet curing with initiator and multi-functional cross-linking agent. The hydrogel may preferably include a buffer system to help prevent discoloration of the hydrogels and/or hydrolysis of the hydrogels and/or to improve shelf-life.

Other additives may be incorporated into the present hydrogels either before or after curing (e.g., conductivity enhancers, pharmaceuticals, humectants plasticizers, etc.) depending on intended end-use. An additive that is preferably added to the hydrogel is a conductive adhesive matter that serves to allow the conductive fluid to both attach patch 10 to the skin of the subject and to serve as the conductive interface between the electrode and the skin. The adhesive additive is preferably a polymeric adhesive and may be pressure or temperature activatable or it may be activated by the exposure to the ambient atmosphere.

In one embodiment, the hydrogel is sufficiently cohesive, yet remains readily separable. Further details pertaining to hydrogels suitable for use in the context of the present invention are described in, for example, U.S. Pat. No. 5,800,685, which is incorporated herein by reference. In any case, an aqueous conductive fluid in accordance with the teachings of the present invention can typically comprise water, alcoholic/aqueous solutions, at least one salt or any other charged agent and preferably a buffering medium. It is appreciated that non-aqueous conductive fluids may also be employed. The conductive fluids used in conjunction with patch 10 preferably administered by deposition on one or both electrodes. It is appreciated that the conductive fluid may alternatively, or in addition, be administered by topical application to the skin. The term "topical" is used herein to refer to administration of a substance on the surface of the skin or mucosal tissue, which can be applied via direct application (e.g., spreading), via an impregnated porous material or object or by spraying or misting. It will be appreciated that topical application of the fluid to the skin of the subject is typically less precise and, if not done carefully, may inadvertently cause an electrical connection between the electrodes directly through the conductive fluid such that the electric current and the mobilized ions would not pass through the skin.

Figure 2A:
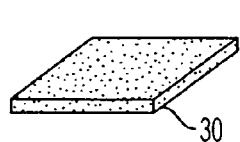
FIG. 2a-g is a cross sectional representation of one embodiment of the substrate.
Figure 2B:
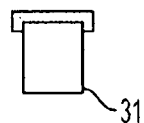
Figure 2C:
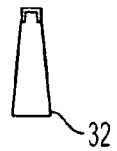
Figure 2D:
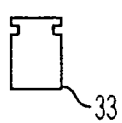
Figure 2E:
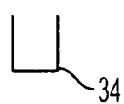
Figure 2F:
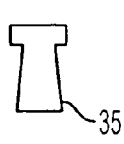
Figure 2G:
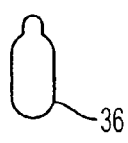
Figure 3A:
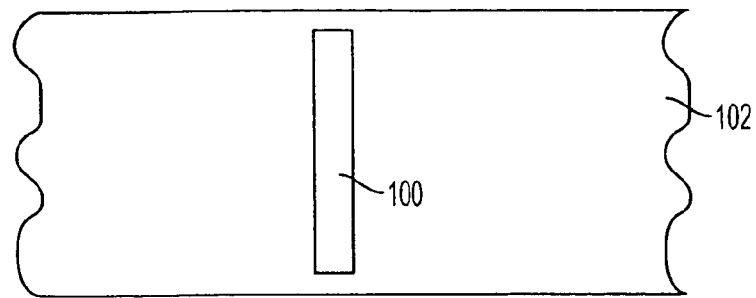
FIGS. 3a-d illustrate a first embodiment according to the present invention.
Figure 3B:
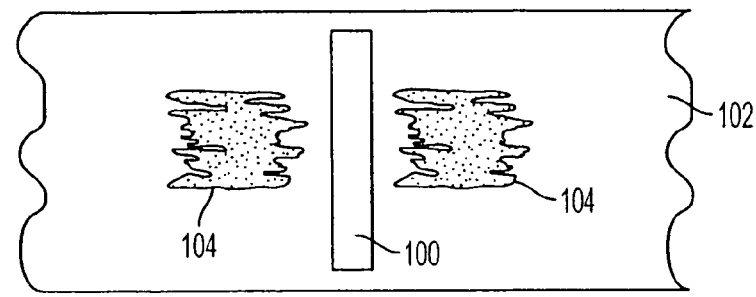
Figure 3C:
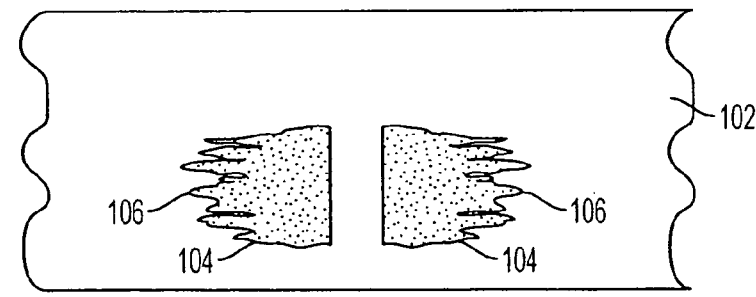
Figure 3D:
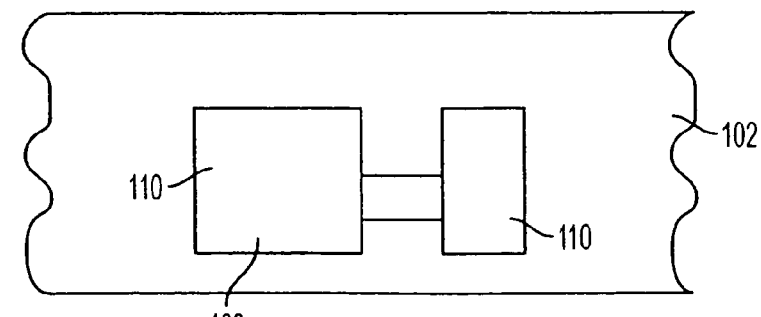
Figure 4A:
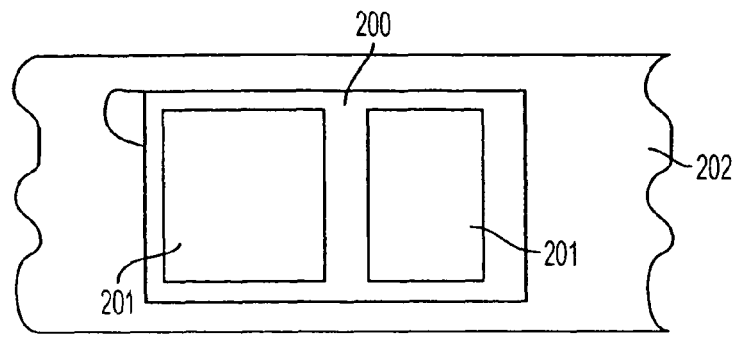
FIGS. 4a-d illustrate a second embodiment according to the present invention.
Figure 4B:
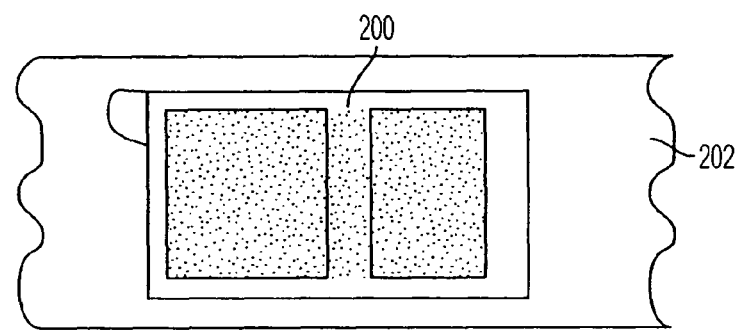
Figure 4C:
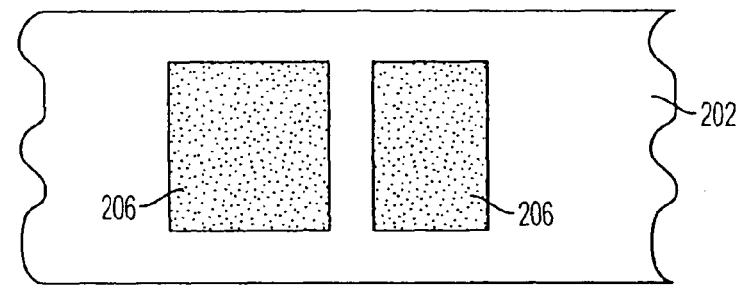
Figure 4D:
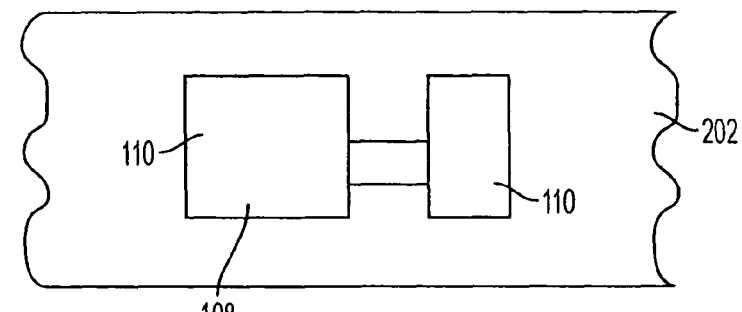

Accordingly, the retainers will vary in shape, size and method of dispensing according to the quantity, application and location relevant to the treatment. Shown in FIGS. 2*b-g* are retainers in the form of a vessel 31 tube 32, a jar 33, a container 34, a dispenser 35 and an ampoule 36. It will be appreciated that the present invention contemplates all such retainers as well as others in any shape, size or configuration that serve to retain the conductive fluid and dispense it for use as needed on either the electrodes or upon the skin of a subject. Shown in FIG. 2*a* is retainer 30 which is a separator. The use of the term "separator" is intended to describe a retainer made of a porous non-conductive material, such as a sponge, paper, etc., that serves to retain the conductive fluid therein. Separators offer advantages over other retainers in that they allow precise positioning of the conductive fluid, they are not messy, and they permit a precise dosage to be administered. It should be noted that a separator can simultaneously act as an electric separator by separating the electrodes 22 and 24 of the device.

Fluid is retained in a separator in such a manner that objects that are in contact with the separator are also in contact with the fluid contained therein. Accordingly, electrical contact may be made with the conductive fluid held within a separator by establishing physical contact between the electrode and the separator. Separators are preferably designed and configured to fit between one or both of electrodes 22 and 24 (FIG. 1) and the skin of the subject, thus providing a simple, clean and convenient electrode/skin interface through which electricity may flow via the conductive fluid to the area of treatment. As stated earlier, separators are constructed so that their non-conductive structure does not impede the electrical contact between electrodes 22 or 24 and the conductive fluid therein. It is understood that a separator will not be positioned such that it or its contents create an electrical contact between electrodes 22 and 24. Such positioning will form an electric circuit that does not include the skin of the subject and will frustrate the purpose of the electrical application. Instead, as noted above, the non-conductive separator may act as an electrical separator by electrically separating the electrodes.

Separators may be fabricated in the form of plugs, cartridges or tablets and the like which are designed to be compatible with different shapes, sizes and configurations of electrodes 22 and/or 24. According to one embodiment, retainer 30 is preferably a thin waferlike container, which may be of a desired shape to be compatible with both the area of treatment and the electrode in use. Such separators may preferably be protected by a thin film layer, which will be peeled off immediately prior to use.

Separators may be packaged for storage or use as may be compatible with the preferred embodiment of the kit of the present invention. Separators can also be individually packaged in order to preserve shelf life and to avoid evaporation of the conducting fluid and/or to substance contained therein.

The use of the above described retainers, particularly separator 30 (FIG. 2*a*), are intended to render patch 10 extremely user friendly and almost foolproof in its employment. The wide variation in the designs and configurations of retainers shown are for the purpose of the precise application of the conductive fluid either on the appropriate electrode or topically upon the skin of the subject. For example, a retainer in the form of tube 32 will permit the simple deposition of a dab of conductive fluid precisely on the electrode. A retainer in the form of ampoule 36 will assure correct dosing of the medicament. Dispenser 35 will permit careful and accurate application of conductive fluid to the exact skin portion of the subject. The preferred embodiment of the invention will have separator 30 as the vehicle for the conductive fluid, which can be positioned with precision on either the electrode or on the skin of the subject.

It is appreciated that the precise positioning of the conductive fluid, either upon the relevant electrode or upon the skin of the subject, is critical to the effective conduction of electric current through the skin of the subject. Accordingly, the kit comprising patch 10 and one or more of retainers 30 through 36 will preferably also contain any other implements, instruction, markings, aids or devices that will serve to assist a user to properly apply and position the conductive fluid as required.

Several embodiments with respect to patch 10 of the present invention are shown in FIGS. 3, 4 and 5. In the embodiment of FIGS. 3*a-d*, a strip 100 is placed over the skin 102 and a conductive lotion, gel, cream or the like 104 is applied over the skin 102, such that upon removal of strip 100, two non-contacting zones 106 receptive of a patch 108 constructed and operative in accordance with the teachings of the present invention are formed and patch 108 is applied onto the skin 102, such that the electrodes 110 thereof each being in contact with one of zones 106 so as to avoid a short circuit.

In the embodiment of FIGS. 4*a-d*, a patterning device 200 having two openings 201 is placed over the skin 202 and a conductive lotion, gel, cream or the like 204 is applied over the skin 202, such that upon removal of patterning device 200, two non-contacting zones 206 receptive of a patch 208 constructed and operative in accordance with the teachings of the present invention are formed and patch 208 is applied onto the skin 202, such that the electrodes 210 thereof each being in contact with one of zones 206, so as to avoid a short circuit.

Figure 5A:
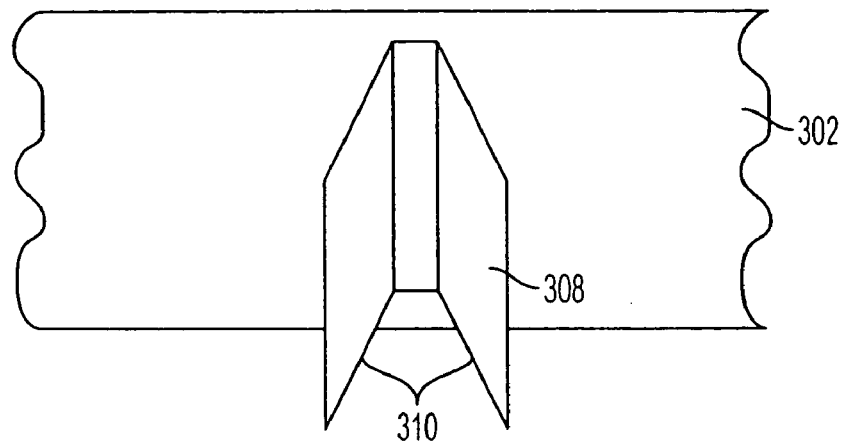
FIGS. 5a-c illustrate a third embodiment according to the present invention.
Figure 5B:
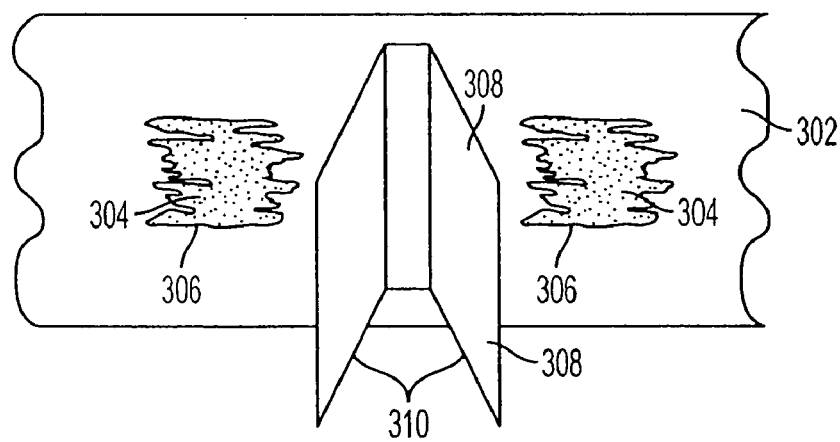
Figure 5C:
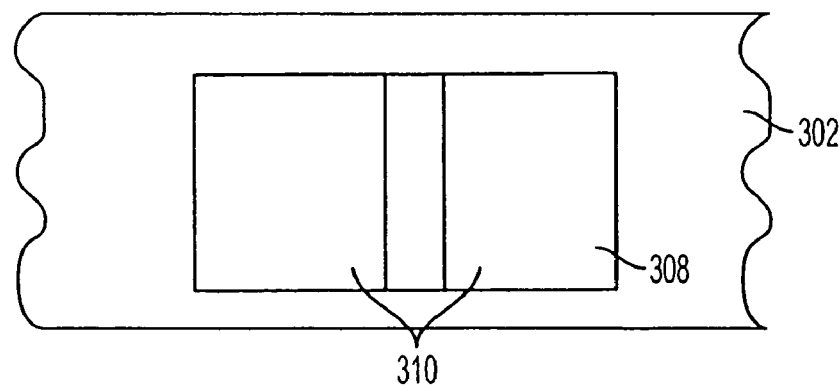

In the embodiment of FIGS. 5*a-c*, a foldable patch 308 is placed, in its folded configuration, over the skin 302 and a conductive lotion, gel, cream or the like 304 is applied over the skin 302 on both sides thereof, such that upon flattening patch 308, two non-contacting zones 306 receptive of patch 308 are formed and patch 308 is contacting the skin 302, such that the electrodes 310 thereof each being in contact with one of zones 306, so as to avoid a short circuit.

Figure 6:
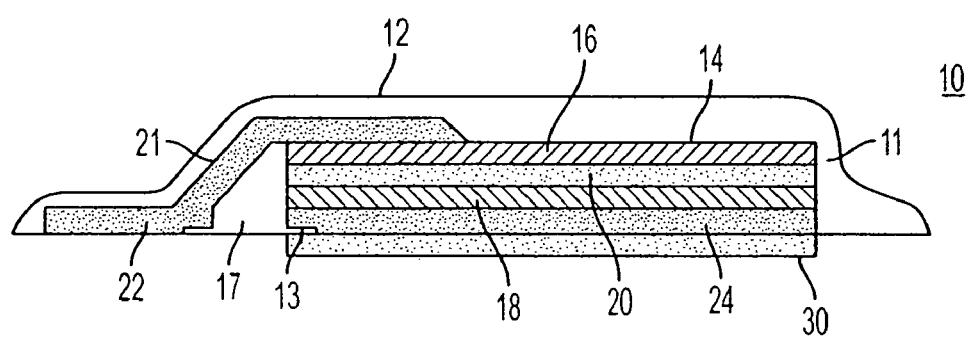
FIG. 6 is a sectional view of another configuration of a dermal patch according to the present invention.

Reference is now made to FIG. 6 which shows an embodiment of patch 10 of the present invention in which electrode 22 is not integral to electrochemical cell 14 but is connected by a conductive connector, hereinafter referred to as connector 21. Components of patch 10 according to this embodiment of the invention and which are similar to those described above, are not further described and are identified by the same reference numerals as above. Connector 21 may be printed or may be of any conductive material known in the art. According to the illustrated embodiment, the retainer, which is a separator, is deposited on electrode 24 of electrochemical cell 14. Thus, in this configuration, electrode 24 may be referred to as the medical electrode and electrode 22 as the conductive adhesive electrode. According to this embodiment, simultaneous contact with the skin of a subject by electrode 22 and separator 30 will form an electrical circuit which includes the skin of the subject as part of the conductive path. In this configuration, electrochemical cell 14 will produce an electric current which will be delivered through the conductive fluid held by retainer 30 which is in contact with the skin. The electric current will pass through the skin thus mobilizing appropriately charged ions or molecules within the conductive fluid contained therein to pass through the skin.

One purpose of patch 10 (FIG. 1) is to transdermally or intradermally deliver a pharmaceutical substance, a cosmetic substance or a cosmeceutical substance. As used herein, the terms "transdermal" and "intradermal" and grammatical variations thereof, respectively refer to the delivery of a composition through/across the skin or into the skin. It is to be understood that the substance to be delivered may be charged prior to or concomitant with its delivery.

As stated, in one embodiment of the invention, the delivery of the substance transdermally or intradermally preferably occurs by a process of iontophoresis, electroosmosis and/or electrophoresis. Iontophoresis refers to the movement of ions caused by the application of an electrical potential. Electroosmosis refers to the convective movement of solvent that occurs through a charged "pore", in response to the preferential passage of counter-ions when the electric field is applied. It is used, for example, as a means to augment the anodic delivery of (in particular) large, positively charged compounds, and to promote the intradermal and transdermal penetration of uncharged, yet polar, molecules. Electrophoresis refers to the movement of charged colloidal particles or macromolecules caused by the application of an electrical field. The electric current caused by the electric potential between electrodes 22 and 24 serves to release the charged substance from the conductive fluid and to deliver the molecules/ions of the charged substance from the conductive fluid and to deliver the molecules into the adjacent skin tissue. The charged substance within the conductive fluid, which is deposited between one or both of electrodes 22 and 24 and the skin of the subject, would be attracted to or repelled by electrode 22 and electrode 24 as appropriate to their charge. For example, if the substance were positively charged, electrode 22 would repel the substance, thus mobilizing it into or through the skin. In this configuration, when current flows from positive electrode 22 in a direction toward the skin, the charged substance is driven across the conductive fluid/skin interface into the skin.

It must be noted that reverse iontophoresis may also be used in a process of transdermal or intradermal recovery of substances from the body. Such a technique employs the same electrical principles applied in reverse. Techniques of transdermal, or intradermal recovery of substances are well known in the art.

The movement of substances transdermally or intradermally may also be aided by a process of electroporation. Electroporation is typically carried out by high voltage pulses applied to a pair of electrodes, which are applied to a tissue surface. The electric pulses cause the passing ions to perforate the tissue layer, providing new pathways for the passage of substances, both charged and not charged. It must be noted that electroporation does not deliver a charged substance, but rather reduces the resistance to passage of substances into the adjacent tissue. Because it does not provide a needed driving force, it is desirable that electroporation be combined with delivery techniques such as iontophoresis or electrophoresis in order to achieve good penetration.

In one embodiment of the invention, the patch is designed so as to facilitate the delivery of an active substance to a desired depth into the subject's body. In particular, the patch is designed to facilitate the delivery of an active substance into the skin, with minimal delivery through the skin.

When a formulation including an active substance is applied onto a subject's skin by iontophoresis, the depth to which the active substance penetrates the subject's body is influenced by a number of different parameters. First, it is influenced by the current density and voltage used to cause iontophoresis. Second, it is influenced by the properties of the formulation, such as its pH, viscosity, conductivity, adhesiveness, concentration of the buffer, and concentration of the electrolyte and most importantly, the concentration of the active substance in the composition. Third, where a substrate including pores is used to hold the formulation (i.e., where a separator in the form of such a substrate is utilized), it is influenced by the size and density of the pores of such substrate, and the physical dimensions of the substrate. Finally, it is influenced by the amount of time that the iontophoresis process is allowed to proceed. For each of these variables, a range of operable values can be determined, and within each range of operable values a preferable, narrower range of values can be obtained. Additional factors that may affect the penetration depth of active substances into the skin (but not through the skin) include the current's wave form, pulses and bi-phasal application. That is, the current can be applied in pulses, as multi-phase current or simply in different wave forms to allow its penetration into the skin with minimal delivery through the skin.

One way to attempt to adjust these parameters to achieve depth control is to modify one or more of them during the iontophoresis process itself. For example, if an appropriate control element were present in an iontophoresis device, the current density or voltage could be adjusted during the operation of the device. This has a couple of drawbacks.

First, as noted above, such control elements can be expensive and potentially bulky, and thus defeat the purpose of a flexible, wearable patch.

Second, it would be difficult for the user of such a device to know exactly what level of current density or voltage will enhance the delivery of the active substance to the target depth. In other words, the user does not know whether the active substance is being delivered into the skin or through the skin, and thus would not know how to adjust the current density or voltage to achieve the desired result.

The inventors have discovered that these drawbacks can be overcome by, for any specific active substance, determining the combination of parameters that will result in maximum delivery of that active substance to the target depth as part of the process of designing the patch itself, and then incorporating that combination of parameters into a patch, formulation and substrate intended to be used together. In this way, for that active substance, a customized patch may be designed that will deliver the active substance to the target depth without the need for a separate control element.

In one mode of practicing the invention, the current density and voltage to be supplied by the electrochemical cell of the patch is selected to provide the desired penetration depth for a previously selected specific formulation including a particular active substance, as well as a previously selected substrate. The formulation has a known pH, viscosity, adhesiveness, conductivity, and active substance concentration, while the pore size, pore density and other properties of the substrate are known as well. Compositions to be applied on such substrate can be in many forms including, but not limited to, liquids, solutions, lotions, creams, pastes, emulsions, gels, soap bars, sprays or aerosols. It would be apparent to those of ordinary skill in the art of cosmetics and dermatology that additives to such compositions may be selected from but are not limited to the group consisting of water, surfactants, emulsifiers, diglycerides, triglycerides, stabilizing agents, thickening agents, alpha-hydroxy carboxylic acids, antioxidants, preservatives, moisturizers, petroleum, mineral oil, glycerol, ethanol, propanol, isopropanol, butanol, polymeric gelling agents, flavoring, colorant and odorant agents and other formulation components, used in the art of pharmaceutical and cosmetic formulary. Such compositions may be applied onto the substrate or directly onto the electrode, according to their physical properties, manually, or using various application devices.

In another mode of practicing the invention, the active substance may be included in a conductive hydrogel attached to one of the electrodes. Such hydrogel has the capacity to adhere to the skin surface, conduct electrical current and release the active substance into the skin. As above, the current density and voltage to be supplied by the electrochemical cell of the patch is selected to provide the desired penetration depth for a previously selected specific formulation including a particular active substance, as well as a previously selected hydrogel. The hydrogel formulation has a known pH, viscosity, adhesiveness, conductivity, and concentration of active substance.

The ideal voltage and/or current density (i.e., the voltage and current density that achieves the desired penetration of the active substance) to be used in combination with that formulation and that substrate, is then determined experimentally (see below). This voltage and current density is then incorporated into a customized patch to be used in combination with the formulation and the substrate/hydrogel by carefully choosing the components of the electrochemical cell to be included in the patch.

In this way, the desired voltage and/or current applied to each electrode can be adjusted to enable penetration of any particular active substance to a desired depth when the patch is used for a standard period of time. While some portions of the active substance may penetrate beyond the desired depth (i.e., penetrate through the skin), selection of a suitable electrochemical cell with the desired voltage/current given the properties of the cosmetic formulation and the substrate/hydrogel can result in a substantial portion of the active substance remaining in the skin.

In another mode of practicing the invention, all of the parameters that can affect the depth to which the active substance is delivered are adjusted during the design process (instead of just adjusting the voltage and the current density to determine the combination of those two parameters that work best with a previously selected formulation and substrate/hydrogel), so that the patch, the formulation including the active substance, and the substrate/hydrogel incorporate that combination of parameters in a way that will maximize the delivery of the active substance to the desired depth when the patch is used during a standard period of time.

One can design a device directed to deliver an active substance mainly into the skin and determine whether more of an active substance has been delivered into the skin than through the skin with an in-vitro skin penetration study. Such a study enables one to determine which combination of parameters results in the maximum amount of an active substance being delivered into the skin with minimal delivery through the skin.

One type of skin penetration test can be implemented in-vitro by using excised swine skin membrane with two electrodes placed thereon, with one of the two being associated with a formulation including an active substance to be delivered by iontophoresis, as described, for example in: P. Glikfeld, C. Cullander, R. S. Hinz, and R. H. Guy, *A new system for in vitro studies of iontophoresis*, Pharm. Res. 5: 443-446 (1988) (hereinafter, the "dual chamber in-vitro test"). Description of the experimental design of an in-vitro skin penetration test is provided in Example No. 1. In a non-limiting way, any of the following parameters can be varied and tested with this model: voltage, current and current density, concentration of an active substance, pH, viscosity, concentration of a buffer, concentration of an electrolyte, concentration of a polymeric substance which is used to render certain rheological properties, conductivity, viscosity and adhesiveness. The influence of pore size and density of a substrate can also be assessed in a modified in-vitro skin penetration test. Delivery of the active substance into and through the skin will be determined as a function of the time of current passage.

In order to obtain an improved selection of the above parameters, a dedicated patch-sealed, mono-cell skin penetration test system (hereinafter, the "patch-sealed chamber test") can be employed. The patch-sealed chamber test comprises a receiving compartment, filled with a receiving vehicle, capable of dissolving an active substance, covered by a sheet of excised human or swine skin and sealed from above by an actual patch pole (either the anode or cathode), having the designated configuration parameters, in intimate contact with a formulation containing an active substance. The patch pole is linked to an externally controlled and monitored power supply, which is also linked to the receiving compartment via an electrical cord. Electrical current is then applied for a set period of time, which is an acceptable time of treatment for the intended cosmetic or medical disorder. Upon conclusion of said period of time, the skin is extracted and the extract is analyzed, using suitable analytical means, such as HPLC or gas chromatography for determination of active substance concentration. If radiolabeled active ingredients are used in the formulation, the analysis can be carried out using radiological assays. The concentration of the active agent in the receiving compartment is also analyzed and the ratio between the amount retained in the skin and the amount detected in the receiving compartment is calculated. An optimal treatment system, according to the present invention is such, that the ratio between the amount retained in the skin and the amount detected in the receiving compartment is maximized.

Thus, the dedicated patch-sealed chamber test enables selecting both formulation parameters (e.g., concentration of an active substance, pH, viscosity, concentration of a buffer, concentration of an electrolyte, concentration of a polymeric substance which is used to render certain Theological properties, conductivity, viscosity and adhesiveness), and patch parameters (e.g., electrical current direction and size, voltage, pore size and density) at the same time.

Based on the results of the study for a given formulation (or a group of formulations with differing concentrations of active substance), the appropriate parameters for that formulation and substrate can be determined. Thus, through pre-selecting the controllable variables using tests designed to determine the ideal combination of variables, the present invention achieves depth-controlled penetration into the skin without the need for a control element.

In a further embodiment, an additional method of increasing skin penetration while minimizing transdermal delivery has been developed. It is known that the main impediment in the passage of electrical current through the skin is attributed to the dead keratin layers of the stratum corneum (SC). These layers, which are relatively dry, possess low electrical conductivity and consequently inhibits the electromotive forces of the iontophoretic device. As illustrated in all textbooks, because of the high impedance of the stratum corneum, electrical current has to pass through the deeper layers of the skin, i.e. the lower epidermis and the dermis, thereby, carrying active agents into the deep layers and subsequently, into the systemic circulation. Thus, it is understood that improving SC conductivity should result in more electrical current passing through the SC and consequently, higher delivery of the active agent into the skin, rather than through the skin. Inducing conductivity by exposing the skin to electrolyte solution is possible. However, it would result in elevated concentrations of cations and anions, which in turn would compete with the active agent and finally inhibit its skin bioavailability. We have discovered that certain skin hydrating agents are capable of inducing SC conductivity, without adding high concentrations of electrolyte. Such agents comprise urea, glycerol, propylene glycol, phospholipids, alpha hydroxy carboxylic acids (e.g., lactic acid and glycolic acid) and beta hydroxy carboxylic acids (e.g., salicylic acid), and mixtures and combinations thereof. Other SC hydrating agents, known in the art of cosmetology can be used as well. SC hydrating agents (a single one or a combination of) can be included in the formulation in concentrations of 2% to 25% by weight of the final formulation. It has been demonstrated in human studies, for example, that addition of 4% urea and 5% propylene glycol significantly induced the electrical current passage through the skin for a for a set voltage, compared with a blank formulation, using the same voltage. Importantly, it was also demonstrated that the resulting higher electrical current was not accompanied by higher levels of skin irritation, which strongly suggests that the excess electrical current passed through the upper layers of the skin, rather than through the deeper layers of the epidermis and dermis.

The embodiments of the present invention are particularly useful for delivery of cosmetic and dermatologic active substances, which are intended for the treatment of the skin, and thus should be delivered into the skin but not through it. Example No. 2 demonstrates that by pre-selecting the parameters of the patch, formulation and other components in accordance with the invention, more of an active substance can be delivered into the skin than through the skin, and that more of an active substance can be delivered into the skin than would be through passive diffusion.

The flexible nature of the patch of the present invention furthers the goal of achieving depth control. More particularly, the flexible nature of the patch ensures that all regions on the active electrode will remain in contact with the skin for the entire period of time during which the patch is being used. This is in contrast to the rigid electrodes of iontophoretic machines, in which the entire active electrode may never be in contact with the skin at any one time (such as where the active electrode is momentarily on a roller), and in which different regions on the active electrode are inevitably in contact with the skin for different periods of time. This may lead to the active substance being driven into the skin to different depths at different locations along the skin/electrode interface, depending on how long each location on the skin was in contact with the active electrode.

Since each region of the active electrode is in contact with the skin for the same amount of time when the patch of the present invention is used, the depth to which the active substance is driven into the skin at different locations on the skin/patch interface is more uniform. Of course, when the depth to which the active substance is driven into the skin is more uniform, greater depth control across the entire interface is facilitated.

The patch of the present invention may be used to deliver any active substance to a desired depth, but it is most appropriately used to deliver active substances that are more effective when delivered into the skin with minimal delivery through the skin. Delivery of active substances into the skin is particularly important in the treatment of skin disorders, of either cosmetic or dermatological nature. Such treatment, also referred to herein as "dermal treatment," enables effective influence of such skin disorder, without excessive systemic exposure to the active substance.

The patch of the present invention may be used to deliver almost any active substance. This includes therapeutic substances in all of the major therapeutic areas including, but not limited to, antiinfectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, antiinflammatory agents, antimigraine preparations, antimotion sickness preparations such as scopolamine and ondansetron, antinauseants, antineoplastics, antiparkinsonism drugs, cardiostimulants such as dobutamine, antipruritics, antipsychotics, antipyretics, antispasmodics; including gastrointestinal and urinary, anticholinergics, sympathornimetics, xanthine derivatives, cardiovascular preparations including calcium channel blockers such as nifedipine, beta-blockers, beta-agonists such as salbutamol and ritodrine, antiarrythmics, antihypertensives such as atenolol, ACE inhibitors, diuretics, vasodilators, including general, coronary, peripheral and cerebral, central nervous system stimulants, cough and cold preparations, decongestants, diagnostics, hormones such as parathyroid hormone, growth hormone and insulin, hypnotics, immunosuppressives, muscle relaxants, parasympatholytics, parasympathomimetics, anti-oxidants; nicotine, prostaglandins, psychostimulants, sedatives and tranquilizers. The patch of the present invention is particularly useful for the delivery of cosmetic and cosmeceutical substances, since those are more effective when delivered into the skin but not through the skin. Such substances, include, for example, skin acting anti-oxidants, such as caretenoids, ascorbic acid (vitamin C) and vitamin E, as well as other vitamin preparations and other anti-oxidants; anti wrinkling agents such as retinoids, including retinol (vitamin A alcohol), alpha-hydroxic acids, beta-hydroxy acid, better known as salicylic acid, combination-hydroxy acids and poly-hydroxy acids, and hydrolyzed and soluble collagen and others; moisturizers such as hyaluronic acid and others; anticellulite agents.

It is understood that the invention may be used for delivery of a wide range of dosages of the above listed and other substances over a desired duration of time.

Active substances for the treatment of skin disorders of dermatological nature may be selected from the group comprising antibiotic, antibacterial, antifungal, antiviral, anesthetic, analgesic, antiallergic, corticosteroid, retinoid, antihistamine, sulfur, immunosuppressant and antiproliferative medications, and mixtures thereof at any proportion. The concentration of said active substances may be adopted to exert a therapeutic effect on a disease when applied to an afflicted area.

Examples of skin disorders of cosmetic nature are set forth in the following list: aging skin, dry skin, sun damaged skin, wrinkles, age spots, various hyperpigmented spots, melasma, puffy eyes, acne, redness of the skin, telangiectasia, cellulite, and obesity. It is also useful in inducing decorative cosmetics, by bestowing the effect agents such as of tanning agents and make up formulation and fixing tattoo inks within the skin layers.

Examples of skin disorders of dermatological nature, as well as active substances which may be used to treat them, are set forth in Table 1.

TABLE 1

A non-exhaustive listing of dermatological disorders, suitable for usage of the iontophoretic system of the present invention and exemplary drugs for such disorders.

| Dermatological Disorder | Exemplary Active Substance |
|---|---|
| Dermatitis | Steroidal and non-steroidal anti-inflammatory agents |
| Contact Dermatitis | |
| Atopic Dermatitis | |
| Seborrheic Dermatitis | |
| Nummular Dermatitis | |
| Chronic Dermatitis Of The Hands And Feet | |
| Generalized Exfoliative Dermatitis | |
| Stasis Dermatitis | |
| Bacterial Infections Of The Skin | Antibiotic and anti-inflammatory agents |
| Cellulitis | |
| Acute Lymphangitis | |
| Lymphadenitis | |
| Erysipelas | |
| Cutaneous Abscesses | |
| Necrotizing Subcutaneous Infections | |
| Staphylococcal Scalded Skin Syndrome | |
| Folliculitis | |
| Furuncles | |
| Hidradenitis Suppurativa | |
| Carbuncles | |
| Paronychial Infections | |
| Erythrasma | |
| Fungal Skin Infection | Antifungal agents |
| Infections caused by dermatophytes--fungi that invade only dead tissues of the skin or its appendages (stratum corneum, nails, hair) | |
| Infections of skin (usually of moist, occluded, intertriginous areas), skin appendages, or mucous membranes caused by yeasts of the genus *Candida*. | |
| Viral Skin Infection | Antiviral agents |
| Warts | |
| Herpes | |
| Disorders of the Hair Follicles And Sebaceous Glands | Keratolytic agents Antibiotics Anti-inflammatory agents Sulfur |
| Acne | |
| Rosacea | |
| Perioral Dermatitis | |
| Hypertrichosis | |
| Alopecia | |
| Pseudofolliculitis Barbae | |
| Keratinous Cyst | |
| Scaling Papular Diseases | Steroidal and non-steroidal anti-inflammatory agents Anti-proliferative agents |
| Psoriasis | |
| Pityriasis Rosea | |
| Lichen Planus | |
| Pityriasis Rubra Pilaris | |
| Pigmentation Disorders | Melanin synthesis inhibitors and enhancers |
| Hypopigmentation | |
| Hyperpigmentation | |
| Scars | Retinoids (e.g., retinoic acid) Alpha and beta hydroxy acids |
| Warts | Keratolytic agents |
| Benign Tumors | Keratolytic agents |
| Moles | Antibiotics |
| Dysplastic Nevi | Anti-inflammatory agents |
| Skin Tags | |
| Lipomas | |
| Angiomas | |
| Pyogenic Granuloma | |

TABLE 1-continued

A non-exhaustive listing of dermatological disorders, suitable for usage of the iontophoretic system of the present invention and exemplary drugs for such disorders.

| Dermatological Disorder | Exemplary Active Substance |
|---|---|
| Seborrheic Keratoses | |
| Dermatofibroma | |
| Keratoacanthoma | |
| Keloid | |
| Malignant Tumors | Various anticancer agents |
| Actinic keratosis (pre-cancer condition) | Photodynamic therapy agents and precursors (e.g., porphirins and ALA) |
| Basal Cell Carcinoma | |
| Squamous Cell Carcinoma | |
| Malignant Melanoma | |
| Paget's Disease Of The Nipples | |
| Kaposi's Sarcoma | Nonsteroidal anti inflammatory drugs (NSAID) |

Treatment according to the present inventions may be beneficial in all body areas. Being thin, flexible and versatile in shape and form, the devices of the present invention can be designed to fit any area of the body and to have any desirable size, according to the area having the disorder.

While the principles of the invention have been discussed in relation to exemplary embodiments discussed herein, it is understood that the principles of the invention are not limited thereto.

Example NO. 1

The "Dual Chamber In-Vitro Test"

Example No. 1 was devised to define, in a preclinical study, the optimal iontophoretic parameters for the delivery of an active substance contained in a cosmetic carrier into the skin, while minimizing systemic exposure.

In general, the active agent is formulated in a buffered, conducting solution, gel, cream, or any other optional cosmetically acceptable carrier. Competing ions are kept to a minimum. Iontophoresis is performed in vertical diffusion cells [1], in which the skin membrane separates the physically- and electrically-isolated anode and cathode chambers from the receptor phase, or in modified side-by-side cells of a newer design. The anode and receptor compartments contain physiologically-buffered saline at pH 7, while the cathode compartment is charged with the gel containing the active.

The skin membrane is from the porcine ear (Alternatively, human (cadaver) or nude mouse skin can be used). The skin is excised with a dermatome set to an approximate depth of 500 µm. The area of skin exposed in each electrode compartment is 0.64 cm$^2$.

The electrodes transmitting the electrical current are made of Ag/AgCl or graphite, prepared in a customary fashion. A constant current is passed between the electrodes and controlled by a custom-built power supply (Professional Design and Development Services, Berkeley, Calif.).

In each study, preparation, with electrical current ("Iontophoretic System") and without electrical current ("Control"), are tested. Exposure period is 20-30 minutes. Six replicates are performed per experiment. Prior to each experiment, the viability and integrity of skin barrier function is checked via a measurement of transepidermal water loss (TEWL).

At the end of the exposure period, the entire receptor compartment is drained and the solution reserved for subsequent analysis of the active agent(s) ("Active"). The skin is removed, and the surfaces carefully cleaned and dried. Subsequently, the stratum corneum ("SC") beneath the cathode chamber is removed by repeated 15 adhesive tape strippings ("TS"). The Active is extracted from the respective tapes and assayed to yield a total uptake of the compound into the SC. The remaining SC-stripped skin from beneath the cathode is then appropriately treated so as to recover the Active, which had crossed the SC barrier, during iontophoresis, and reached into the underlying epidermis/upper dermis. The Active is determined quantitatively using customary analytical procedures (e.g., HPLC, UV spectrum, GC, radiolabeled detection, etc.), as applicable.

Example NO. 2

Results of an In-Vitro Skin Penetration Test for Magnesium Ascorbyl Phosphate (MAP) Aqueous Solution, Using the "Dual Chamber In-Vitro Test"
Parameters:
Active Substance: Magnesium Ascorbyl Phosphate (MAP) (Vitamin C Derivative)
Concentration: 3%
Carrier: Distilled water
Amount Applied: 25 mg
pH: 7.0-7.4
Electrical Current: 0.150 mA/cm$^2$
Exposure Period: 30 minutes
Skin: Porcine, ear
Detection: HPLC

TABLE 2

Iontophoretic System A

| | Amount of Active, in μg | | | | Summary Table | |
| --- | --- | --- | --- | --- | --- | --- |
| | | | | | Total TS # 3-15 + | Total TS # 3-15 + |
| Cell No. | TS #1, 2 (μg) | TS #3-15 (μg) | TS Total (μg) | Viable Skin (μg) | Receptor (μg) | Viable Skin (μg) | Viable skin (μg/cm2) |
| 1 | 92.41 | 89.22 | 181.63 | 33.94 | 47.66 | 123.16 | 183.82 |
| 2 | 50.37 | 2.94 | 53.31 | 4.55 | 122.75 | 7.49 | 11.18 |
| 3 | 103.88 | 115.27 | 219.15 | 56.67 | 14.62 | 171.94 | 256.63 |
| 4 | 132.28 | 43.90 | 176.18 | 8.44 | 23.47 | 52.34 | 78.12 |
| 5 | 48.43 | 8.71 | 57.14 | 19.24 | 24.99 | 27.95 | 41.72 |
| 6 | 89.89 | 50.43 | 140.32 | 10.30 | 25.43 | 60.73 | 10.89 |
| Mean | 73.77 | 42.06 | 115.82 | 23.07 | 43.15 | 65.13 | 97.21 |
| S.D. | 37.16 | 41.40 | 72.03 | 16.96 | 40.51 | 58.36 | 87.10 |

TS = Tape Strippings

B. Passive Control
In a parallel Passive Control experiment, the mean total amount found in tape strippings #1-15 was in the same order of magnitude, as found in the above study (separate analysis for TS#1,2 and TS#3-15 was not performed). Yet, the mean amount found in the viable skin, which is the target organ for biological activity was 1 μg only, significantly lower than for the Iontophoretic System. The mean amount found in the receptor was 2 μg.
Conclusion
(1) For the Iontophoretic System, the mean amount of Active in the viable skin is in biologically relevant levels, unlike the respective amount in the Passive Control system (23 μg vs. 1 μg respectively).
(2) For the Iontophoretic System, the amount in the skin (TS#3-15+ Viable skin) is higher than the amount transferred through the skin, using the selected electrical parameters and carrier (65 μg vs. 43 μg respectively).
(3) For the Iontophoretic System, the total amount found in the skin (TS#1-15+ Viable skin) is higher than the amount transferred through the skin, using the selected electrical parameters and carrier (139 μg vs. 43 μg respectively).

Another purpose of patch 10 is to promote wound healing, scar reduction, scar prevention, tissue repair and/or tissue regeneration by direct application of currents through the skin. Electric current has long been known and utilized therapeutically to force excitable cells (nerve, muscles and receptors of nerve ends) of the human body, by electrical stimuli externally supplied in the form of electrical pulses, to generate an electrical response, the so-called action potentials. These action potentials are cell-intrinsic electrical pulses with a defined amplitude and duration for the relevant cell type. For one nerve, for instance, a pulse width of about 1 ms and an amplitude of about 80 mV to 100 mV is typical. The cell reverts to its cell membrane voltage, which at rest, depending on cell type, has a value between 60 mV and 120 mV. This voltage is caused by different ion concentrations in the extracellular and intracellular spaces separated by the cell membrane. More positive ions are found outside the cell. According to definition, the potential outside the cell is set to 0 V, so that a negative potential is given in the cell.

In healthy humans, the action potentials are generated by the body itself and utilized for information transfer and to trigger cellular processes. In electrotherapy, therapeutic effects are induced by specific generation of action potentials (defined number and at specific loci).

Apparatuses for electrotherapy use a plurality of various electrical currents, or pulse forms. Aiming to choose the electrotherapy best suited for a specific indication, the therapist should be able to revert to criteria of maximally clear definition. These criteria derive from the replies, to questions about the effectiveness and tolerance of the various current form.

The spectrum of effects includes, e.g., the areas of pain alleviation, stimulation of striated and nonstriated muscles, of influencing perfusion, the detumescent mechanisms, of the areas of checking inflammatory processes and of promoting regeneration (wounds, accelerated healing of bones, etc.). The aim in the application should always be achieving the desired effect in the affected area by proper selection of the current form, either distal or, proximal to the electrode or in the depth of the body.

Basically, electrotherapeutic apparatuses are based on two stimulus current methods, the polarity-dependent "polar stimulation principle" and the polarity-independent "apolar stimulation principle".

Low-frequency alternating currents (LF current) ranging from 0 to 200 Hz are used in the "polar stimulation principle". Hyperpolarization (rise in membrane voltage) occurs beneath the positive electrode, the anode, making the spacing between the potential in the cell and the stimulus threshold greater. In contrast, the membrane voltage drops beneath the negative electrode, the cathode. As the stimulus threshold is reached, the cell triggers automatically an action potential.

Stimulant current apparatuses employ different pulse shapes in the low-frequency spectrum of about 0 to 200 Hz (LF current). Applicable are, e.g., the so-called delta currents, rectangular currents, diadynamic currents, high-voltage currents, ultrastimulant currents, Faraday currents—to name a few. Some alternating currents have a direct current component, which additionally backs the polar effects. There are two frequency-dependent methods of using action potential's therapeutically:

First, functional imitation principle—The number of action potentials generated by the excitable cell (e.g., nerve or muscle) for the performance of its tasks is ascertained. In therapy, the same number of pulses are then generated in the relevant cell by stimulation, thereby backing the cell in performing its tasks. For instance, a stimulation frequency of up to 6 Hz is applied to generate up to 6 individual contractions per second.

Second, fatigue principle—In contrast, when forcing the cell (nerve or muscle) to generate action potentials, by stimulation at higher frequency and appreciably more often than the cell would be required to do so to perform its tasks, it fatigues after a short time. The opposite effect occurs. The cell fatigue can be explained by energy-consuming processes in the formation of action potentials. For instance, a sclerosed muscle can be relaxed according to this principle by stimulating it with a "higher" frequency of; e.g., 100 Hz or 200 Hz.

To generate any action potentials the intensity must be chosen sufficiently high to exceed the stimulus threshold. The level of intensity to be set depends on the following factors: the position (depth) of the cell to be stimulated in the tissue (distance from the electrode), the size of the electrodes and the tissue resistances in the region penetrated by the electric potential, which, in turn, is influenced by the parameters of the current form.

In practice, current form and electrode size are prescribed. To stimulate now a group of cells at a certain distance from the electrode (for example, deep in the tissue), the current and/or voltage intensity continues to be increased until action potentials occur.

As the intensity increases, cells located deeper, and deeper, or cells ever more distal from the electrodes, are being stimulated successively. With the apolar stimulation principle, only so-called medium-frequency alternating currents (MF currents) without any direct current component are employed. Meant by MF currents are sinusoidal alternating currents with a frequency of >5 Hz to 100,000 Hz. A single cycle (alternating pulse) with sufficient intensity has a polar effect which is able to trigger an action potential in a nerve or muscle cell.

Often, a "summation effect" occurs. At increasing frequency, ever higher intensities are also needed in order to be able to trigger action potentials in the cells. Wyss has proved beyond doubt that the generation of action potentials with MF pulses proceeds entirely independently of polar effects. This means that wherever the intensity and number of oscillations is sufficiently large, action potentials will be generated irrespective of the momentary polarity of the MF current (Wyss, Oscar A. M.: Prinzipien der elektrischen Reizung, [Principle of Electrical Stimulation], Neujahrs-Blatt, published by the Natural Research Society in Zurich for the year 1976, Kommissionsverlag Leeman A G, Zurich, 1976, 28-34).

MF pulses are applied at a low-frequency repetition rate of 0 to about 200 Hz and MF carrier frequencies of >5 Hz to 100,000 Hz. In practice, this may be a sinusoidal, square-wave, triangular-wave, or other amplitude-modulated MF current (AM-MF current). The following principles are in agreement with those described in conjunction with the "polar stimulation principle".

Functional-imitation principle: In synchronism with the MF pulses (amplitude modulation), action potentials occur in excitable cells. The cell is thereby induced to exercise its natural functions, which emanate from this frequency.

Fatigue principle: To fatigue excitable cells, MF pulses with higher amplitudes are used. As the current intensity rises, cells are stimulated successively that are located deeper and deeper (more distal from the electrodes). Along with an increasing the frequency, more intensity is needed to generate action potentials.

On the basis of the medium-frequency alternating current, the following additional options of therapy are given: When stimulating with (constant-amplitude) MF current of sufficient intensity, an action potential is generated first. With MF current that flows for a longer time, the decaying flank of the action potential remains at the depolarization level (permanent depolarization), which amounts to about one-half of equilibrium potential. Upon shutting the NM current off, the membrane voltage drops then, delayed, to the level of equilibrium potential.

The following sub-items describe the therapeutic utilization of the permanent depolarization.

Pain alleviation and influencing perfusion: High intensities which, depending on the properties of the region being treated, range at the tolerance limit, cause a blocking of nerve transmission paths, due to the permanent depolarization. This genuine nerve block (proof established by BOWMAN, Bruce R., 1981, dissertation E. K. University of LJubljana, Rancho Los Amigos Hospital, Downey, Calif., U.S.A.) is utilized, e.g., for pain blocking in phantom-limb pains or for stellatum block in blood flow disorders.

Muscular contraction: Muscle training in voluntary innervation insufficiency and muscle distention. With the nerve muscle apparatus intact; the striated muscle (skeletal muscle) is stimulated directly by permanent depolarization. This results in muscle contraction, which is used, e.g., in; voluntary innervation insufficiency of the muscles or to stretch the antagonists of spastic muscles. During treatment, the intensity should be interrupted by pauses in short intervals. The intensity also may be increased and decreased between 100% and about 50% of the adjusted value.

Generating strong muscle contraction forces: Very strong muscle contractions may be induced without fatigue phenomena. In tetanic contraction, which can be induced with stimulation current of about 50 Hz and up, a rapid decrease of the muscle contraction force occurs contrarily, due to fatigue of the myokinetic units.

Cell division: Wound healing and accelerated bone healing. Permanent depolarization induces cell division in healthy cells. Wound healing may be promoted thereby, bone healing accelerated in fractures. Moreover, MF currents induce under the effect of the electrical alternating field reciprocal movement (shaking effect) of charged molecules in the current penetrated tissue, accompanied by rotation movements of the charged molecule shares. Achieved thereby is a greater probability of a "correct" meeting position of enzyme and substrate, which, in metabolic processes, interact chemically (metabolic facilitation). This shaking effect tends to level differences in concentration, in that diffusion processes which on account of existing concentration gradients proceed in certain directions are accelerated due to the kinetic energy that is additionally imparted (MF iontophoresis, inhibition of inflammation, alleviation of pain). The shaking effect is especially effective at high intensities.

Distribution of inflammatory and pain mediators: Inhibition of inflammation and alleviation of pain. In painful, inflammatory processes a high concentration of inflammatory and pain mediators is regularly found in the diseased tissue. This high concentration is reduced (dispersed) by the shaking effect. Caused by high current intensities, the "shaking intensity"—the same as the frequency—is of great significance for the therapeutic effects (Hans-Jurgens, May, Elektrische Differential-Therapie [Electrical Differential Therapy], Karlsruhe 1990).

Influencing of metabolism (diffusion, mitochondria, cyclic AMP): Facilitation and promotion of metabolic processes. As described above, the biochemical metabolic processes are facilitated. Also in penetrating cell cultures with MF current (frequency >5 Hz to 100,000) it has been found that the number of mitochondria ("energy plants" of the cells) and their size increase significantly. The concentration of an important messenger substance of the cell, the cyclic AMP, can also be influenced by alternating current, depending on MF current and/or voltage (Dertinger, 1989, Kemforschungszentrum Karlsruhe, Nagy Nemectron GmbH Karlsruhe).

Furthermore, a painless and strong muscle contraction can be induced with MF currents. The so-called "threshold dissociation" occurs from 8 kHz, that is, the threshold amperage for muscle contraction goes below that of the sensible threshold (Edel, H.: Fibel der Elektrodiagnostik and Elektrotherapie [Primer of Electrodiagnostics and Electrotherapy, Muller & Steinicke Munchen 1983, p. 193). Strong muscle contractions can be induced without pain. Viewed therapeutically, threshold dissociation is of particular interest in utilizing the reversible process of muscle contraction, which is caused by the permanent depolarization of the MF current.

Due to the high intensities of the MF current, heat is generated in the current-penetrated tissue. But a prerequisite is that the patient not be discomforted by exceeding the thresholds (sensation, muscle, tolerance, pain).

Analogous to the improvement of the metabolic processes, also an iontophoresis can be accomplished with MF current, i.e., the administration of medications with the aid of current through the skin into the body. Owing to the physical circumstances, iontophoresis with MF current requires a longer treatment time and higher intensities as compared to galvanic current.

As described above and found insofar also in the pertaining trade 5 literature (refer to book "Elektrische Differential-Therapie" [Electrical Differential Therapy] by A. Hansjuorgens and H. U. May, 1990; Nemectron GmbH, Karlsruhe), the prior electrotherapeutic apparatuses employ, depending on diagnosis, low-frequency currents or amplitude-modulated medium-frequency currents at frequencies 0 to 200 Hz or medium-frequency currents at a frequency of >5 Hz to 100,000 Hz, each with constant amplitude (intensity).

Because any one and more of the above uses is anticipated for dermal patch of the present invention, patch 10 preferably includes electrical circuitry for controlling the level or duration of current produced by electrochemical cell 14. Such circuitry may take the form of an on-off switch for "on-demand" drug delivery (e.g., patient controlled delivery of an analgesic for pain relief), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of electric current since a constant current level ensures a constant rate of substance delivery. The level of current can be controlled by a variety of known means, for example, a resistor or a simple circuit that employs a resistor and a field effect transistor. The circuitry may also include an integrated circuit which could be designed to control the dosage of active agent delivered, or even to respond to sensor signals in order to regulate the dosage to maintain a predetermined dosage regimen. A relatively simple circuit can control the current as a function of time, and if desired, generate complex current waveforms such as pulses or sinusoidal waves as is further described above. In addition, the circuitry may employ a bio-feedback system which monitors a biosignal, provides an assessment of the therapy, and adjusts the active agent delivery accordingly. A typical example is the monitoring of the blood sugar level for controlled administration of insulin to a diabetic patient. A simple yet important use of a controlling circuit is the avoidance of heat buildup and resultant tissue damage. It is understood that the delivery of ions causes heat due to the movement of the ions and that the greater the delivery, the greater will be the heat buildup at the site of the delivery. As such, the current used for treatment could be patient-controlled such that a balance may be found between maximizing the delivery of substance and minimizing the discomfort of temperature increase.

Example NO. 4

Reference is now made to the following example, which further illustrates the invention in a non-limiting fashion.

Treatment of mild rosacea—Mild rosacea, characterized by redness of parts of the face and telangectasia, is a common disorder, afflicting many individuals, mainly from the aging population. Unfortunately the treatments for mild rosacea are limited. Five patients with mild rosacea were enrolled in a pilot study, meeting the following inclusion criteria: Patient had mild to moderate redness in both sides of the face; and Patient was between 20 and 65 years of age.

The study objectives were to detect the therapeutic effects on the redness phenomenon, during and following treatment and to detect side effects. Each study subject received treatment of both sides of the face. On one side of the face an iontophoretic patch", linked to a thin and flexible power supply so that the large part of the patch (main patch) was linked to the positive pole of the power supply and the small part of the patch (counter-patch) was linked to the negative pole of the power supply. A "passive patch", with same shape, without being connected to an electrical source, was used on the other side of the face of each study subject.

Each patch was coated by a Test Preparation (aqueous gel, containing an astringent herbal extract). 0.4 ml of the Test Preparation was evenly applied onto the Main Patch and 0.1 ml to the Counter Patch, using a spatula. The patches were then applied onto the skin of the study subjects for a period of 20 minutes (the Treatment Period). Observations were taken immediately after removal of the patches and 10, 25 and 40 minutes thereafter, including subjective assessment by the patient and blinded assessment by a trained observer. Photographs were taken prior to treatment and at all observation points.

In all five study subjects, there was a pronounced reduction in the degree of redness and the extent of telangiectasia at the Active Patch sites. This improvement was first observed immediately after patch removal and further documented for the rest of the observation period. The Passive control patch sites exhibited very slight improvements, which were not considered by the patients or the observer as significant.

It will be appreciated by persons skilled in the art that the present invention is not limited to what has been particularly shown and described hereinabove. Rather, the scope of the present invention is defined by the appended claims and includes both combinations and sub-combinations of the various features described hereinabove as well as variations and modifications thereof which would occur to persons skilled in the art upon reading the foregoing description. Accordingly, it is intended to embrace all such alternatives, modifications and variations that fall within the spirit and broad scope of the appended claims.

What is claimed is:

1. A flexible dermal patch having a top surface and a skin contacting bottom surface, the patch comprising:
    at least one negative electrode and at least one positive electrode for electrical coupling to the skin portion and/or skin appendage of a subject, wherein the at least one negative electrode and the at least one positive electrode are disposed substantially coplanar on the skin contacting bottom surface and a first electrode of the at least one negative electrode and the at least one positive electrode is disposed on a skin contacting side of the skin contacting bottom surface;
    an internal flexible power source electrically coupled to the at least one negative electrode and the at least one positive electrode, wherein the flexible power source powers the patch and is disposed in or on the patch; and
    at least one separator comprising a porous non-conductive material retaining a conductive fluid/composition therein, said at least one separator disposed on a second electrode of the at least one negative electrode and the at least one positive electrode, the at least one separator being for preventing contact between at least one of the at least one negative electrode and the at least one positive electrode and the skin portion, wherein the first electrode does not include a separator comprising a porous non-conductive material disposed thereon.

2. The flexible dermal patch of claim 1, wherein the at least one negative electrode, the at least one positive electrode and the flexible power source are disposed on a patch body in spaced relation to each other to avoid contact between each of the electrodes.

3. The flexible dermal patch of claim 1, wherein the patch is for treatment of a disorder selected from the group consisting of wrinkles, acne, aging skin, dry skin, pigmentation disorders, age spots, rosacea, puffy eyes, cellulite, warts and psoriasis.

4. The flexible dermal patch of claim 1, wherein the conductive fluid/composition comprises a hydrogel.

5. A kit comprising:
    (a) a flexible dermal patch having a top surface and a skin contacting bottom surface, the patch comprising a power source and at least two substantially coplanar electrodes in electrical connection with the power source, the electrodes for electrical coupling with a skin portion and/or skin appendage of a subject, wherein the at least two electrodes are disposed on the skin contacting bottom surface and a first electrode of the at least two electrodes is disposed on a skin contacting side of the skin contacting bottom surface; and
    (b) at least one retainer comprising at least one separator comprising a porous non-conductive material for retaining a conductive fluid, the conductive fluid being for deposition on a second electrode of the at least two electrodes and/or topical application onto the skin portion and/or skin appendage of the subject, wherein the retainer is for disposing on the second electrode and for preventing contact between the second electrode and the skin portion, wherein the first electrode does not include a separator comprising a porous non-conductive material disposed thereon;
    the patch being designed and configured for delivering an electric current through the skin and the conductive fluid, for introduction of current and/or voltage to the skin portion and/or skin appendage, and/or transdermal or intradermal delivery of at least one substance.

6. The flexible dermal patch of claim 1, wherein the patch is for treating a fungal infection of a nail of a subject, and wherein the conductive fluid/composition comprises an antifungal agent.

7. The flexible dermal patch of claim 6, wherein when the flexible dermal patch is placed on the skin and/or nail of the subject, the at least two electrodes are disposed in spaced relation to each other and are electrically coupled to the skin and/or nail with the conductive composition acting as an interface between at least one of the at least one negative electrode and the at least one positive electrode and the skin and/or nail, and the flexible power source can provide electricity for delivering the antifungal agent to the skin and/or nail for treating the fungal infection.

8. The flexible dermal patch of claim 6, wherein the at least one negative electrode and the at least one positive electrode and the flexible power source are disposed in spaced relation to each other on a patch body.

9. The flexible dermal patch of claim 6, wherein the conductive fluid/composition further comprises a gelling agent with minimal competing ions.

10. The flexible dermal patch of claim 6, wherein the conductive fluid/composition further comprises a stratum corneum hydrating agent.

11. The flexible dermal patch of claim 1, wherein the patch is for treating a fungal infection, and wherein treatment comprises delivery of a substance to a subject, and the fungal infection is an infection of the subject selected from the group consisting of a dermatophyte skin infection, dermatophyte infection of a skin appendage, a dermatophyte infection of a dead tissue of the skin, a dermatophyte infection of the stratum corneum of the skin, dermatophyte infection of a nail, dermatophyte infection of hair, Candida skin infection, Candida infection of a skin appendage, Candida infection of the skin in an occluded area and/or intertriginous area and Candida infection of the skin in a moist area.

12. The flexible dermal patch of claim 6, wherein the fungal infection is a dermatophyte infection of a nail.

13. The flexible dermal patch of claim 6, further comprising electrical circuitry coupled to the dermal patch for controlling the level or duration of an electric current supplied by the flexible power source.

14. The flexible dermal patch of claim 13, wherein the electrical circuitry comprises an integrated circuit configured to control the delivered dosage of the antifungal agent.

15. The flexible dermal patch of claim 6, wherein the dermal patch is wearable.

16. The flexible dermal patch of claim 6, further comprising an attachment mechanism for attaching the dermal patch to the skin.

17. The flexible dermal patch of claim 1, wherein the flexible power source comprises a flexible electrochemical cell.

18. The flexible dermal patch of claim 6, further comprising a removable cover encapsulating the at least one negative electrode, the at least one positive electrode, and the flexible power source.

19. The flexible dermal patch of claim 6, wherein the antifungal agent is delivered by a mechanism selected from the group consisting of iontophoresis, electrophoresis, electroporation, electroosmosis and a combination thereof.

20. The flexible dermal patch of claim 6, wherein the flexible power source is configured for supplying a predetermined constant level of electric current.

21. The flexible dermal patch of claim 17, wherein the flexible electrochemical cell comprises:
a flexible layer open liquid state electrochemical cell which comprises a first layer of insoluble negative pole, a second layer of insoluble positive pole and a third layer of aqueous electrolyte, the third layer being disposed between the first and second layers and including:
(a) a deliquescent material for keeping the open cell wet at all times;
(b) an electroactive soluble material for obtaining required ionic conductivity; and
(c) a water-soluble polymer for obtaining a required viscosity for adhering the first and the second layers to the third layer.

22. The flexible dermal patch of claim 6, wherein the conductive fluid/composition comprises a hydrogel.

23. A kit for treating a fungal infection of the skin and/or skin appendage of a subject, comprising the flexible dermal patch of claim 6, wherein the separator is configured to be attached to the patch before use.

24. The flexible dermal patch of claim 1, further comprising a removable cover encapsulating the at least one negative electrode, the at least one positive electrode, and the flexible power source.

25. The kit of claim 5 for treatment of a fungal infection of the skin and/or skin appendage of a subject wherein the conductive fluid comprises an antifungal agent.

26. The flexible dermal patch of claim 1, wherein the separator is attachable.

27. A method of treating puffy eyes in a subject suffering therefrom comprising: applying the patch of claim 1 to the eye area of the subject; introducing current; and iontophoretically delivering an active substance to the subject to treat the puffy eyes.

28. A method of treating puffy eyes in a subject suffering therefrom comprising:
applying the patch of claim 1 to the eye area of the subject;
iontophoretically delivering the conductive fluid/composition to the subject to treat the puffy eyes.

29. The flexible dermal patch of claim 1, wherein the first electrode comprises a conductive adhesive hydrogel disposed on the skin contacting side thereof.

30. The flexible dermal patch of claim 29, wherein the patch is adapted for contact with the skin by the adhesive hydrogel on first electrode and by the separator on the second electrode.

31. The flexible dermal patch of claim 1, wherein the flexible patch is for treatment of a disorder selected from the group consisting of aging skin, dry skin, sun damaged skin, wrinkles, age spots, various hyperpigmented spots, melasma, puffy eyes, acne, redness of the skin, telangiectasia, cellulite, obesity, dermatitis, contact dermatitis, atopic dermatitis, seborrheic dermatitis, nummular dermatitis, chronic dermatitis of the hands and feet, generalized exfoliative dermatitis, stasis dermatitis, bacterial infections of the skin, cellulitis, acute lymphangitis, lymphadenitis, erysipelas, cutaneous abscesses, necrotizing subcutaneous infections, Staphylococcal scalded skin syndrome, folliculitis, furuncles, hidradenitis suppurativa, carbuncles, paronychial infections, erythrasma, viral skin infection, herpes, disorders of the hair follicles and sebaceous glands, rosacea, perioral dermatitis, hypertrichosis, alopecia, pseudofolliculitis barbae, keratinous cyst, scaling popular diseases, psoriasis, pityriasis rosea, lichen planus, pityriasis, rubra pilaris, pigmentation disorders, hypopigmentation, hyperpigmentation, warts, scars, benign tumours, moles, dysplastic nevi, skin tags, lipomas, angiomas, pyogenic granuloma, seborrheic keratoses, dermatofibroma, keratoacanthoma, keloid, malignant tumors, actinic keratosis, basal cell carcinoma, squamous cell carcinoma, malignant melanoma, Paget's disease of the nipples, Kaposi's sarcoma, a fungal infection, pain, inflammation, and a combination thereof.

32. The kit of claim 5, wherein the kit is for treatment of a disorder selected from the group consisting of aging skin, dry skin, sun damaged skin, wrinkles, age spots, various hyperpigmented spots, melasma, puffy eyes, acne, redness of the skin, telangiectasia, cellulite, obesity, dermatitis, contact dermatitis, atopic dermatitis, seborrheic dermatitis, nummular dermatitis, chronic dermatitis of the hands and feet, generalized exfoliative dermatitis, stasis dermatitis, bacterial infections of the skin, cellulitis, acute lymphangitis, lymphadenitis, erysipelas, cutaneous abscesses, necrotizing subcutaneous infections, Staphylococcal scalded skin syndrome, folliculitis, furuncles, hidradenitis suppurativa, carbuncles, paronychial infections, erythrasma, viral skin infection, herpes, disorders of the hair follicles and sebaceous glands, rosacea, perioral dermatitis, hypertrichosis, alopecia, pseudofolliculitis barbae, keratinous cyst, scaling popular diseases, psoriasis, pityriasis rosea, lichen planus, pityriasis, rubra pilaris, pigmentation disorders, hypopigmentation, hyperpigmentation, warts, scars, benign tumours, moles, dysplastic nevi, skin tags, lipomas, angiomas, pyogenic granuloma, seborrheic keratoses, dermatofibroma, keratoacanthoma, keloid, malignant tumors, actinic keratosis, basal cell carcinoma, squamous cell carcinoma, malignant melanoma, Paget's disease of the nipples, Kaposi's sarcoma, a fungal infection, pain, and inflammation.

* * * * *